(12) United States Patent
Ebinger et al.

(10) Patent No.: US 11,110,237 B2
(45) Date of Patent: Sep. 7, 2021

(54) THERAPEUTIC DEVICE FOR RESPIRATORY PASSAGES

(71) Applicant: R. Cegla GmbH & Co. KG, Montabaur (DE)

(72) Inventors: Andrea Ebinger, Montabaur (DE); Ulrich Cegla, Montabaur (DE)

(73) Assignee: R. Cegla GmbH & Co. KG, Montabaur (DE)

( * ) Notice: Subject to any disclaimer, the term of this patent is extended or adjusted under 35 U.S.C. 154(b) by 918 days.

(21) Appl. No.: 15/606,053

(22) Filed: May 26, 2017

(65) Prior Publication Data

US 2017/0348497 A1 Dec. 7, 2017

(30) Foreign Application Priority Data

Jun. 1, 2016 (DE) ................. 16 172 474.5

(51) Int. Cl.
*A61M 16/00* (2006.01)
*A61M 39/10* (2006.01)
(Continued)

(52) U.S. Cl.
CPC .... *A61M 16/0006* (2014.02); *A61M 16/0816* (2013.01); *A61M 16/0875* (2013.01); *A61M 16/208* (2013.01); *A61M 39/10* (2013.01)

(58) Field of Classification Search
CPC ............ A61M 16/0006; A61M 16/208; A61M 16/0816; A61M 16/0875; A61M 39/10; A63B 23/18; A61B 5/087; A61B 5/0876
See application file for complete search history.

(56) References Cited

U.S. PATENT DOCUMENTS 4,264,989 A * 5/1981 Wiley ................. A61F 2/20
623/9
4,557,261 A 12/1985 Rügheimer
(Continued)

FOREIGN PATENT DOCUMENTS

| EP | 2087927 | 8/2009 | |
| EP | 2783728 A1 * | 10/2014 | ............. A63B 23/18 |
| WO | WO 98/24500 | 6/1998 | |

*Primary Examiner* — Joseph D. Boecker
*Assistant Examiner* — Thomas W Greig
(74) *Attorney, Agent, or Firm* — Pandiscio & Pandiscio

(57) ABSTRACT

In a therapeutic device for respiratory passages (1) for the treatment of respiratory problems, comprising at least one pipe section (3) which has at least one passage duct (4) through which air (5) can be inhaled or exhaled and at least one elastic hose (8) with its first free end (9) arranged on one free end on one of the pipe sections (3) and which can vibrate during inhalation or exhalation in one flow direction (6) because of the throughflow, the hose (8) should be able to be exchanged in a straightforward and uncomplicated procedure even by people with restricted finger mobility or manual dexterity.
This task is achieved in that the circumference of the first free end (9) of the hose (8) is smaller than or equal to the circumference of the passage duct (4) of the free end of the pipe section (3), that the width (b) of one of the long sides (14) of the first free end (9) of the hose (8) is larger than the width or diameter (d) of the passage duct (4), that areas of the hose (8) can be inserted into the passage duct (4) by compressing the long side (14) and that the hose (8) is held in the passage duct (4) by a preload force after having been inserted.

10 Claims, 4 Drawing Sheets

(51) Int. Cl.
*A61M 16/08* (2006.01)
*A61M 16/20* (2006.01)

(56) References Cited

U.S. PATENT DOCUMENTS

| | | | |
|---|---|---|---|
| 7,059,328 B2* | 6/2006 | Wood | A61M 16/0666 |
| | | | 128/207.13 |
| 8,826,943 B2* | 9/2014 | Sheffer | A61M 16/0875 |
| | | | 138/118 |
| 2008/0041391 A1* | 2/2008 | Worley | A61M 16/0465 |
| | | | 128/207.14 |
| 2008/0251069 A1* | 10/2008 | Cegla | A63B 21/00069 |
| | | | 128/200.24 |
| 2009/0199853 A1 | 8/2009 | Cegla | |
| 2012/0227741 A1* | 9/2012 | Cegla | A63B 23/18 |
| | | | 128/205.12 |
| 2013/0160888 A1 | 6/2013 | Sheffer | |
| 2013/0186394 A1* | 7/2013 | Hallett | A61M 16/0057 |
| | | | 128/201.13 |
| 2014/0238389 A1 | 8/2014 | Bruggemann et al. | |
| 2016/0045689 A1* | 2/2016 | Cegla | A63B 21/0085 |
| | | | 128/204.25 |

\* cited by examiner

THERAPEUTIC DEVICE FOR RESPIRATORY PASSAGES

REFERENCE TO PENDING PRIOR PATENT APPLICATION

This patent application claims benefit of European Patent Application No. 16 172 474.5, filed Jun. 1, 2016, which patent application is hereby incorporated herein by reference.

FIELD OF THE INVENTION

The present invention relates to a therapeutic device for respiratory passages in accordance with the pre-characterising clauses of patent claim 1.

BACKGROUND OF THE INVENTION

A therapeutic device for respiratory passages of this kind has been disclosed in EP 2 087 927 A1. This therapeutic device for respiratory passages is used for improving the respiration of a person and typically consists of a mouthpiece and a hose that is drawn onto a nozzle on the mouthpiece. Moreover, the hose is surrounded by a convolute or curved pipe section which gives the hose its curvature. During exhalation, the breath is forced into a hose and the hose is induced to vibrate depending on the curvature of the pipe section.

Such therapeutic device for respiratory passages have proven effective in practice in a variety of ways and are used for the therapy of asthma patients with significant respiratory problems and even elite sportspersons for increasing the pulmonary volume and improving the respiratory process.

However, it has proven to be a disadvantage that exchanging the hose requires a certain amount of manual dexterity because the hose is made from an elastic polymer and has tube drawn onto the nozzle of the pipe section or mouthpiece. For this purpose, the hose must initially be expanded so that the hose can subsequently be slid onto the nozzle. In particular, exchanging the hose represents a significant obstacle for patients with restricted finger mobility or low manual dexterity.

SUMMARY OF THE INVENTION

The task of the present invention is therefore to create a therapeutic device for respiratory passages for the treatment of respiratory problems of the aforementioned kind in such a way that its hose can be exchanged in a straightforward and uncomplicated procedure even by people with restricted finger mobility or manual dexterity, with the help of which the patient can train his/her respiratory passages when inhaling and exhaling, so that the desired therapeutic effect can take place.

Furthermore, it is the task of the present invention to provide a therapeutic device for respiratory passages of which the individual components are inexpensive, easy to handle and can be cleaned or sterilised in a user-friendly way.

These tasks are accomplished by the features in the pre-characterising clause of patent claim 1.

Further advantageous configurations of the invention are disclosed in the subordinated claims.

Due to the facts that the circumference of the first free end of the hose is smaller than or equal to the circumference of the passage duct of the free end of the pipe section, that the width of one of the long sides of the first free end of the hose is larger than the width or diameter of the passage duct of the free end of the pipe section, that areas of the hose can be inserted into the passage duct by compressing the long side and that the hose is held in the passage duct by a preload force after having been inserted, the hose can be inserted into the passage duct of the pipe section in a straightforward and uncomplicated manner even by people with restricted finger mobility or manual dexterity. The hose can be inserted manually into the pipe section without undergoing stretching, by means of slightly pressing together or compressing the long sides. After insertion and release, the hose attempts to return to its initial shape as a result of its elastic properties and the long sides are pressed against the passage duct due to the condition of tension.

The hose makes contact with the passage duct with the effect that the exhaled air is directed into the hose and causes it to vibrate as the air flows through the hose.

Furthermore, it has proven to be advantageous for one or more bulges to be arranged on the first free end of the hose, on the side facing the passage duct. The bulges protrude outwardly from the hose and seal the air gap between the hose and the passage duct in the form of a lamellar seal when inserted. As a result, any flow of respiratory air through the air gap between the hose and the pipe section is prevented to the greatest possible extent.

It is advantageous for one or more grooves or shoulders to be worked into or formed onto the area of the first free end of the hose, which also form a lamellar seal between the hose and the pipe section. Furthermore, the grooves can be adapted to the dimensions of the bulges on the hose, with the effect that the bulges on the hose engage in the grooves. This means, firstly, the hose is held in the passage duct by the form-locked connection while, secondly, the arrangement achieves a good sealing effect in the lamellar seal.

In addition, it has proven to be advantageous for the passage duct to be divided into several passage duct branches by at least one passage duct branchings. Each of the passage branches has a valve arranged in it which establishes the flow direction in the particular passage duct branch. Consequently, a hose can be inserted in each of the passage duct branches in accordance with the flow direction, with the result that passage duct branches have air flowing through them alternately due to the valves during inhalation and exhalation, and the corresponding hose vibrates.

In an advantageous embodiment, the hose is configured as a flat hose or oval shaped hose. The passage duct, on the other hand, is rotationally symmetrical and the width of the flat hose is larger than the diameter of the passage duct.

The first free end of the hose can also have an oval shape, in which case the circumference of the hose is less than or equal to the circumference of the passage duct and the widest long side of the hose is larger than the diameter of the hose or vice versa.

BRIEF DESCRIPTION OF THE DRAWINGS

The drawing shows one sample embodiment and two further embodiment variants configured in accordance with the present invention, the details of which are explained below. In the drawing.

DETAILED DESCRIPTION OF THE PREFERRED EMBODIMENTS

Figure 1A:
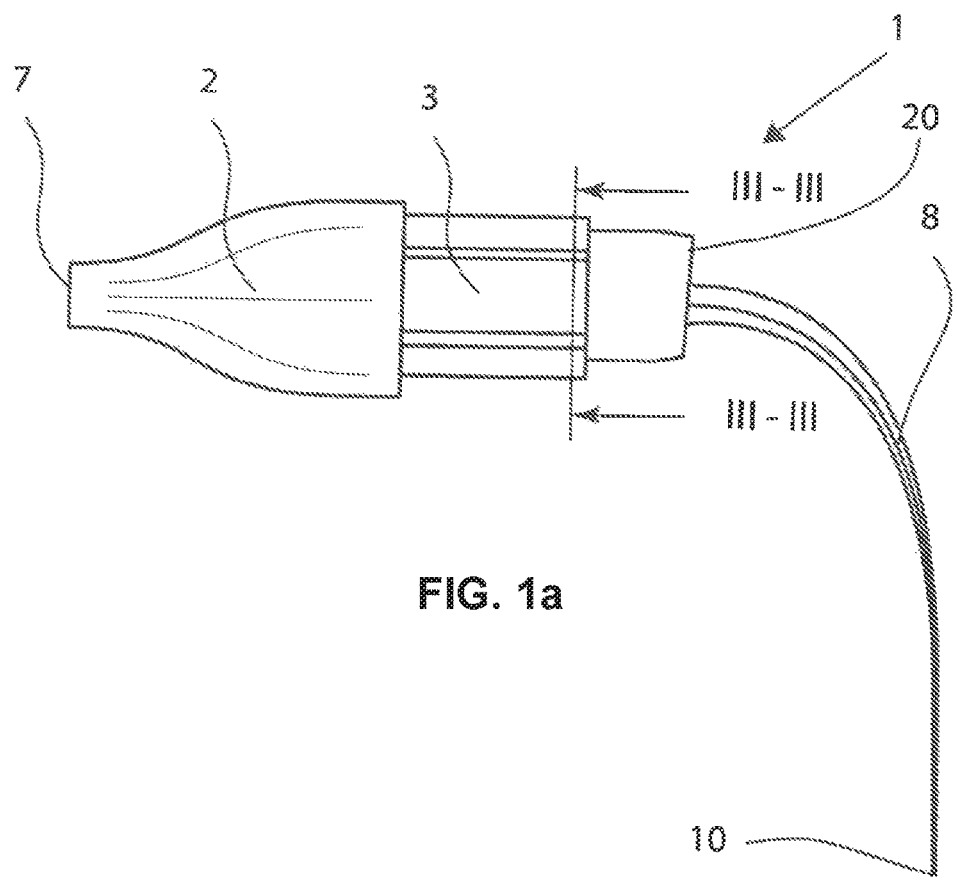
FIG. 1a shows a therapeutic device for respiratory passages with a pipe section that forms a passage duct on the first free end of which a mouthpiece is worked or formed and a hose is inserted in the passage duct of the second free end.

FIG. 1a shows a therapeutic device for respiratory passages 1 for improving the respiration of a patient which is formed from a pipe section 3. The pipe section 3 has a cylindrical passage duct 4 on its inside with a diameter d. The first free end of the pipe section 3 has a mouthpiece 2 attached to it which, firstly creates an oral support for the therapeutic device for respiratory passages 1 which is comfortable for the patient, and secondly forms an opening for the passage duct 4. On the side 20 of the pipe section 3 facing away from the mouthpiece 2, a hose 8 is partially guided or inserted into the passage duct 4.

Figure 1B:
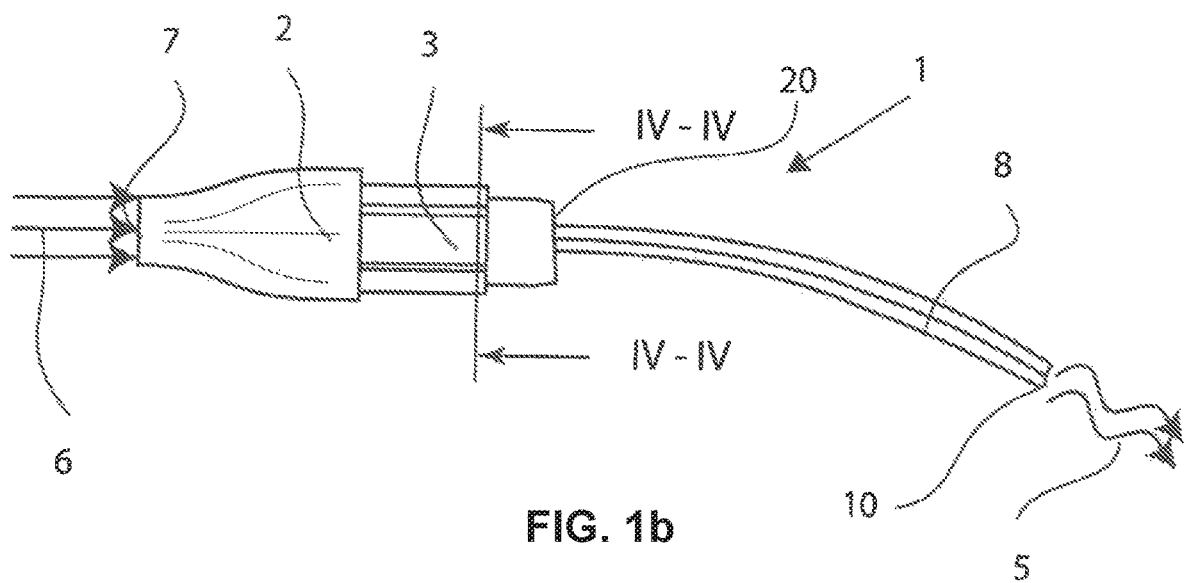
FIG. 1b shows the therapeutic device for respiratory passages in accordance with FIG. 1a, in which respiratory air is blown in the flow direction through the mouthpiece and the hose is caused to vibrate.

FIG. 1b shows the therapeutic device for respiratory passages 1 in the actuated condition. Respiratory air is forced into the passage duct 4 through the opening 7 of the mouthpiece 2 in one flow direction 6. The respiratory air 5 flows through the passage duct 4 and enters the hose 8 through this. The air 5 expands the hose 8 if the air flow is sufficient, and induces an oscillatory vibration in the hose 8.

To allow the hose 8 to be assembled without complications even by patients with restricted finger mobility and to prevent it from slipping out inadvertently during use, the hose 8 is held by a force and/or form-locked connection or by preload force in the passage duct 4, as shown below in FIGS. 2a to 5. After the therapeutic device for respiratory passages 1 has been used, the hose 8 can be pulled out of the passage duct 4 for cleaning purposes or for disposal with only a small amount of effort.

Figure 2A:
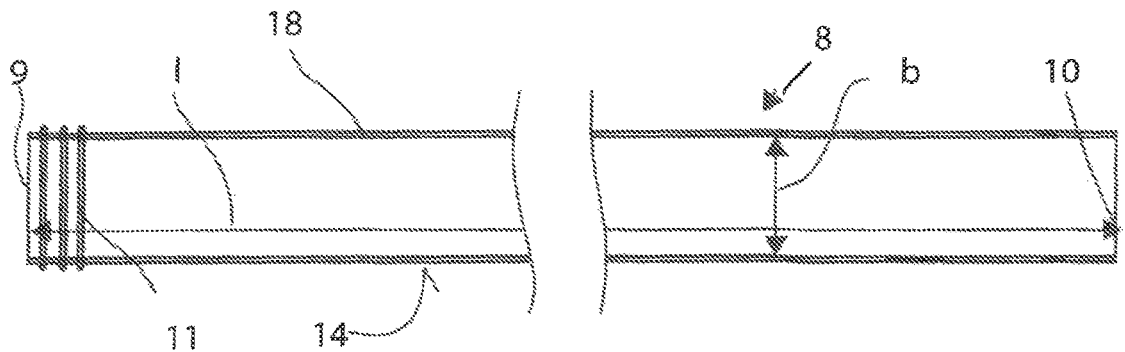
FIGS. 2a and 2b show a plan view and a side view, respectively, of the hose in accordance with FIG. 1a, FIG. 3 shows a cutaway view across the flow direction in accordance with FIG. 1a, FIG. 4 shows a cutaway view across the flow direction in accordance with FIG. 1b.
Figure 2B:
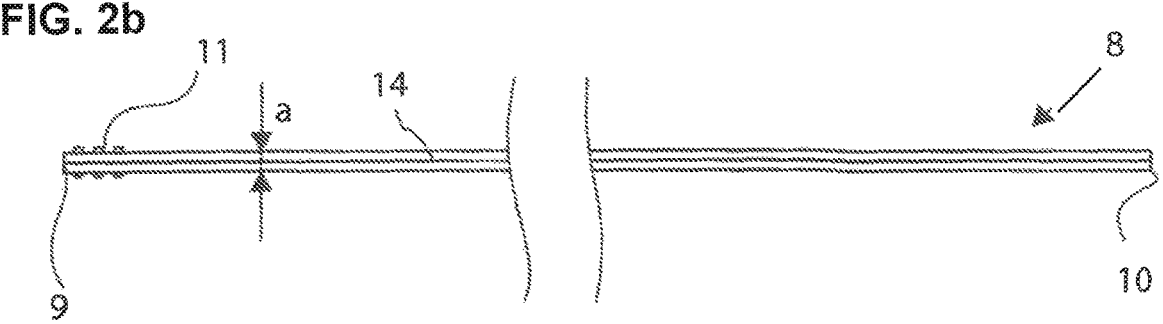

For this purpose, and as shown in particular in FIGS. 2a and 2b, the hose 8 is formed as a flat hose 8 or an oval hose (b>>a) with several bulges 11 formed or worked onto its first free end 9. Along both long sides 14, a hose seam 18 connects the lower and upper halves of the flat hose 8 to one another. The insides of the hose 8 are provided with a parting agent which prevents the two insides of the hose 8 from sticking together.

The hose 8 is manufactured from an elastic material, preferably silicone. The width b—the distance between the two long sides 14—of the hose 8 is larger than the diameter d of the passage duct 4 and the length l of the hose 8 corresponds to the multiple of its width b.

Figure 3:
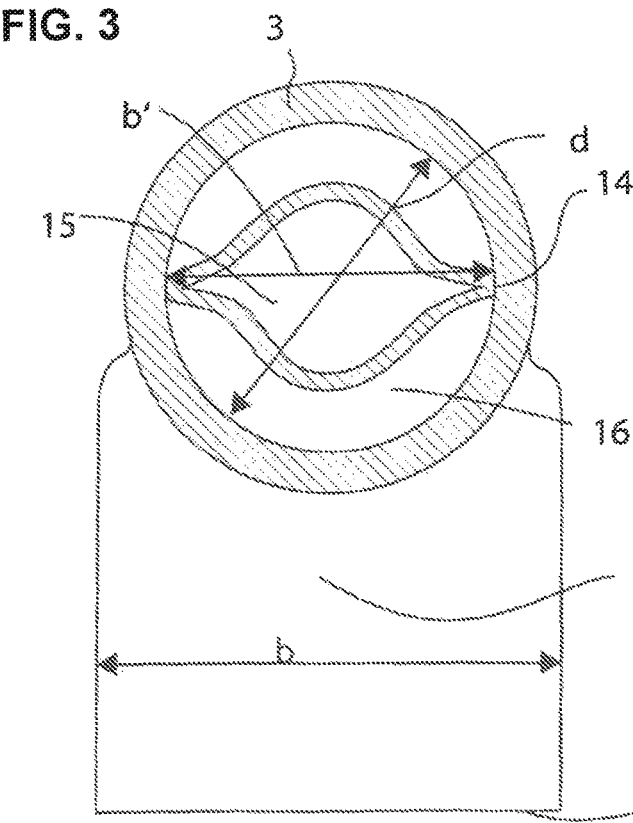
Figure 4:
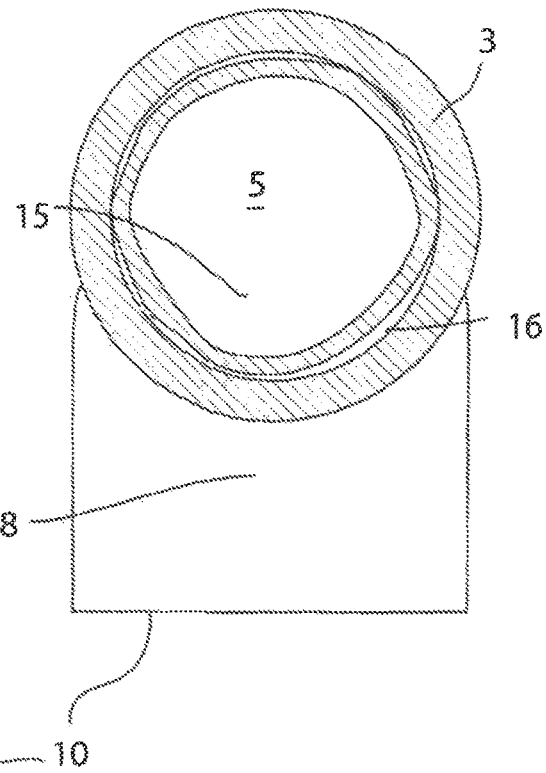

The flat hose 8 is compressed at the first free end 9 for inserting into the passage duct 4, with the effect that the width b' of the flat hose 8 is then smaller than the diameter d of the passage duct (b>d>b'). An area of the hose 8 is then inserted or guided into the passage duct 4 and, as soon as it is released, the hose 8 attempts to return to its original shape because of its elastic properties. However, the diameter d of the passage duct 4 is smaller than the width b of the hose 8 in its initial condition, which means the long sides 14 of the hose 8 are pressed against the two opposite sides of the passage duct 4, as a result of which the force or friction-locked connection between the pipe section 3 and the hose 8 is established as shown in FIG. 3. The two long sides 14 of the first free end 9 of the hose 8 are thus in contact with the passage duct 4 in areas in the inserted condition.

For this purpose, the hose 8 must be manufactured at least from an elastic material and possess an adequate rigidity I. The preload force which forms the force-locked connection between the hose 8 and the passage duct 4 must be of sufficient magnitude to hold the hose 8 in the passage duct 4 even at high flow rates or maximum respiratory air pressure.

Typically, the first free end of the hose 8 is inserted into the passage duct 4 by between 0.25 d and 2 d, although this dimension value can vary significantly depending on numerous factors. Significant parameters are the preload force as a function of the elasticity and rigidity (El) if the hose 8, the insertion depth and the friction between the hose 8 and the passage duct 4.

The compression of the long sides 14 before insertion of the flat hose 8 into the passage duct 4 means the upper and lower sides on the first free end 9 are separated from one another and a blow-in opening 15 is formed in the hose 8. During exhalation, and as shown in particular in FIG. 4, the hose 8 is completely opened by the throughflow and is pressed against the passage duct 4.

As a result of the configuration of the hose 8, there remains a slight air gap 16 between the hose 8 and the passage duct 4 because the circumference of the hose 8 is smaller than the circumference of the passage duct 4. In order to seal this air gap 16 in the most effective possible way, several bulges 11 are formed onto the side of the hose 8 facing the passage duct 4 and they seal the air gap 16 in the most effective possible way according to the method of a lamellar seal 13.

Figure 5:
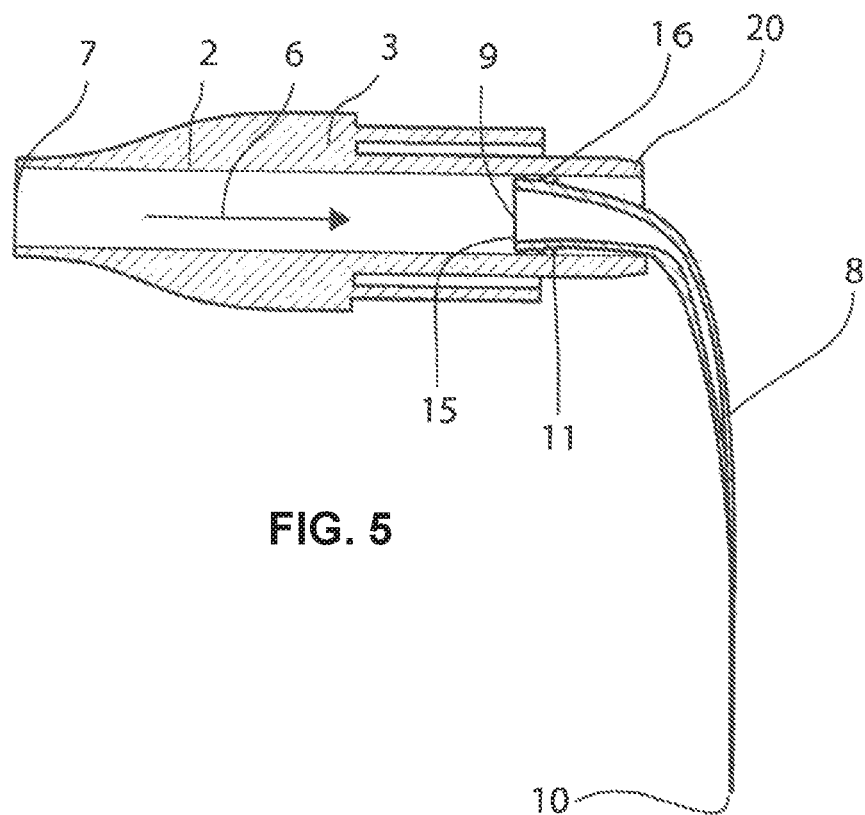
FIG. 5 shows a cutaway view across of the therapeutic device for respiratory passages in accordance with FIG. 1a, FIG. 6 shows a cutaway view of a second embodiment variant in accordance with FIG. 1a with grooves worked into the passage duct into which bulges projecting from the hose engage

In particular in FIG. 5, it can be seen that the hose 8 must be pushed at least sufficiently far into the passage duct 4 until all the bulges 11 are in contact with the passage duct 4. The insertion depth can additionally be indicated by markings on the hose 8.

Figure 6:
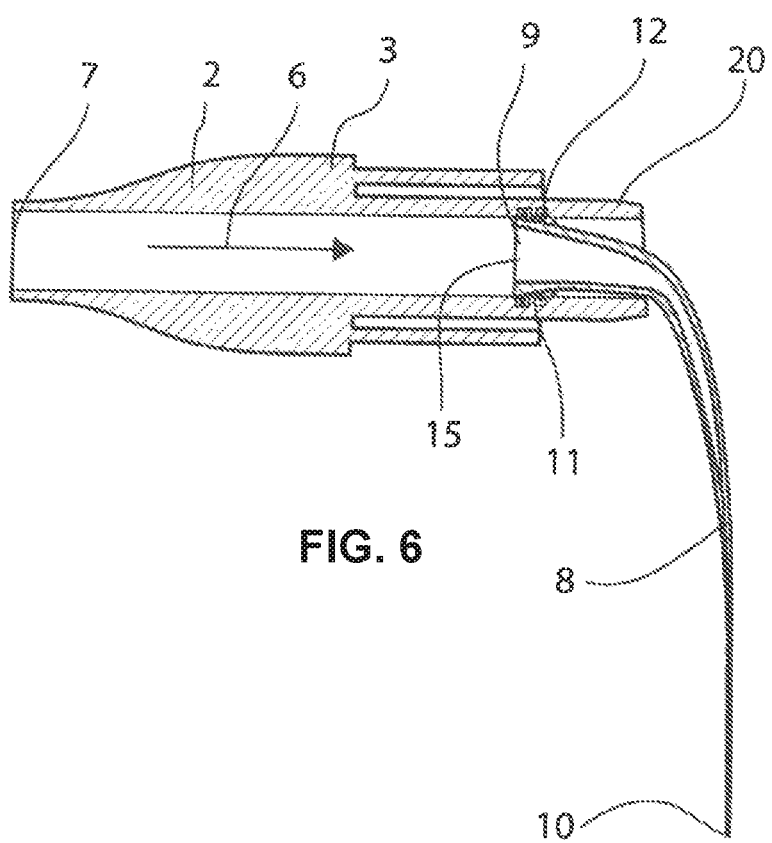

FIG. 6 shows a further embodiment variant of the therapeutic device for respiratory passages 1 in which the passage duct 4 has several grooves 12 worked into it. The grooves 12, firstly, form the lamellar seal 13 of the air gap 16 between the passage duct 4 and the hose 8. Secondly, they can be adapted to the dimensions of the bulges 11 on the hose 8 with the effect that the bulges 11 engage in the grooves 12 when the hose 8 has been inserted. As a result, a form-locked connection is formed in addition to the force-locked one.

Consequently, the hose is held, firstly, by the preload force which presses the two long sides 14 against the two opposite sides of the passage duct, and secondly, by the form-locked connection between the bulges 11 and the grooves 12.

In a straightforward arrangement, the grooves 12 can also be configured as shoulders 17 which project from the pipe section 3 into the passage duct 4. The shoulders 17 can, firstly, form a stop for the hose 8 and/or secondly form the lamellar seal 13.

Alternatively, the passage duct 4 of the pipe section 3 can be configured in a conical arrangement with its diameter d continuously increasing at the second free end, with the effect that the hose 8 can be clamped in this during insertion.

Figure 7:
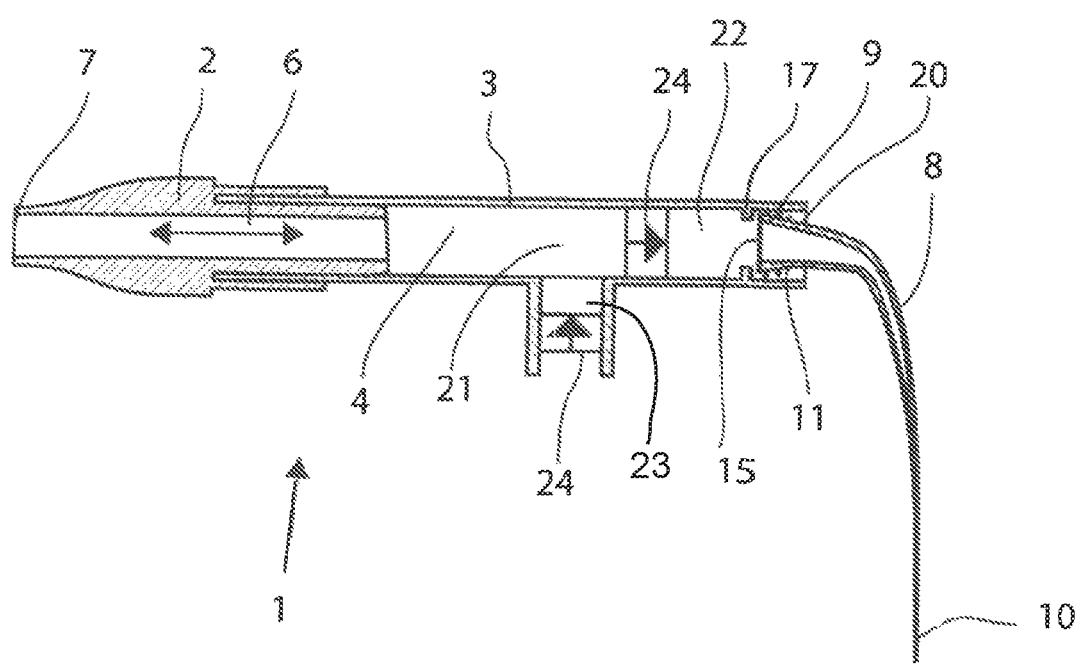
FIG. 7 shows a third embodiment variant of the therapeutic device for respiratory passages in accordance with the present invention with one passage duct branch and two valves, each of which allow air to flow through the particular duct branch during inhalation and exhalation and vice versa.

FIG. 7 shows a second embodiment variant of the therapeutic device for respiratory passages 1 in accordance with the present invention. The therapeutic device for respiratory passages 1 is formed from a plurality of pipe sections 3 which are interconnected in a modular arrangement. Each of the pipe sections 3 has a plug-and-socket arrangement 25 which makes it possible for two pipe sections 3 to be connected together making an airtight seal.

A passage duct branching 21 is arranged in one of the pipe sections 3 which divides the passage duct 4 into a first and a second passage duct branch 22, 23. The pipe section 3 is placed on the mouthpiece 2 by means of the plug-and-socket arrangement 25 and it has two valves 24 which provide one flow direction 6 for the particular passage duct branch 22, 23. Accordingly, when exhaling through the valves 24, the first passage duct branch 22 is open and the respiratory air 5 is channeled through the first passage duct branch 22 to the hose 8. During inhalation, the valve 24 closes in the first passage duct branch 22 and the valve 24 in the second passage duct branch 23 is opened so that the patient can both exhale and inhale using the therapeutic device for respiratory passages 1.

In a straightforward manner, a second hose 8 can be arranged in the second passage duct branch 23 with its free end 10 in the passage duct 4 directed towards the mouthpiece 2.

The first free end 9 of the hose 8 can have a conical configuration with the effect that the inlet opening 15 of the hose 8 is slightly opened and possesses an opened inlet opening 15. the hose 8 or its first free end 9 thus has an oval cross section (a<b), in which case the width b of the hose 8 is greater than the diameter d of the passage duct 4 (b>d) and the circumference of the hose 8 is less than or equal to the circumference of the passage duct 4 (2×b≤π×d).

The passage duct 4 can also have non-rotationally symmetrical cross sectional shapes, e.g. rectangular, triangular or the like. In particular, and in a straightforward manner, oval cross sections are possible with a width:height ratio (a:b) which can be adapted to the opening ratio of the patient's mouth.

It is significant that the circumference of the first free end 9 of the hose 8 is smaller in dimension that the inner circumference of the pipe section 3 or than the circumference of the passage duct 4 and the width b of one of the long sides 14 of the hose 8 is larger than the distance between the possible contact points of the long sides 14 of the hose 8 in the passage duct 4. The contact points are arranged on two opposite sides of the passage duct, and a line connecting the two points intersects the centroid of the area of the passage duct.

What is claimed is:

1. A therapeutic device for respiratory passages for the treatment of respiratory problems, comprising:

at least one pipe section which has at least one passage duct through which air can be inhaled or exhaled at least one elastic hose with its first free end arranged on one free end on one of the pipe sections and which can vibrate during inhalation or exhalation in one flow direction because of the throughflow, characterised in that, the circumference of the first free end of the hose is smaller than or equal to the circumference of the passage duct of the free end of the pipe section, that the width of one of the long sides of the first free end of the hose is larger than the width or diameter of the passage duct, that areas of the hose can be inserted into the passage duct by compressing the long side and that the hose is held in the passage duct by a preload force after having been inserted.

2. The therapeutic device for respiratory passages in accordance with claim 1, characterised in that, one or more bulges are arranged on the first free end of the hose on the side facing the passage duct and that the bulges form a lamellar seal in the passage duct.

3. The therapeutic device for respiratory passages in accordance with claim 2, characterised in that, one or more grooves are worked into the passage duct in the area of the first free end of the hose and that the grooves in the passage duct form the lamellar seal between the hose and the pipe section.

4. The therapeutic device for respiratory passages in accordance with claim 3, characterised in that, the groove is adapted to the dimensions of the bulge on the hose, that the bulge engages in the groove and that the hose is held in the passage duct by the form-locked connection between the bulge and the groove.

5. The therapeutic device for respiratory passages in accordance with claim 1, characterised in that, the first free end of the hose has a funnel shape and that an inlet opening is formed by the funnel shape.

6. The therapeutic device for respiratory passages in accordance with claim 1, characterised in that, the passage duct is subdivided into several passage duct branches by at least one passage duct branching, that a valve is arranged in each of the passage duct branches and that the valve establishes the flow direction in the particular pipe sections.

7. The therapeutic device for respiratory passages in accordance with claim 6, characterised in that, a hose is inserted in each of the passage duct branches and that air flows alternately within two of the passage duct branches during inhalation and exhalation because of the valve, causing the hoses in the two passage duct branches to vibrate alternately.

8. The therapeutic device for respiratory passages in accordance with claim 1, characterised in that, the hose is formed as a flat or oval-shaped hose.

9. The therapeutic device for respiratory passages in accordance with claim 1, characterised in that, the hose is manufactured from silicone.

10. The therapeutic device for respiratory passages in accordance with claim 1, characterised in that, a mouthpiece is arranged on one of the pipe sections.

* * * * *